United States Patent [19]

Bowen

[11] Patent Number: 5,872,147
[45] Date of Patent: Feb. 16, 1999

[54] USE OF OXANDROLONE IN THE TREATMENT OF CHRONIC OBSTRUCTIVE PULMONARY DISEASE

[75] Inventor: Robert E. Bowen, Martinsburg, W. Va.

[73] Assignee: Bio-Technology General Corp., Iselin, N.J.

[21] Appl. No.: 986,015

[22] Filed: Dec. 5, 1997

Related U.S. Application Data

[60] Provisional application No. 60/032,107 Dec. 5, 1996.
[51] Int. Cl.$^6$ ................................................... A61K 31/335
[52] U.S. Cl. ............................................ 514/453; 514/174
[58] Field of Search .................................... 514/453, 174

[56] References Cited

U.S. PATENT DOCUMENTS

| | | | |
|---|---|---|---|
| 3,128,283 | 4/1964 | Pappo | 514/453 |
| 4,039,668 | 8/1977 | Fuchs et al. | 514/177 |
| 4,376,733 | 3/1983 | Frimer | 549/268 |
| 4,914,106 | 4/1990 | Shibata et al. | 514/453 |
| 5,096,916 | 3/1992 | Skupin | 514/401 |

OTHER PUBLICATIONS

Desforges, Current Concepts, vol. 328, pp. 1017–1022, 1993.
New England J. of Med., pp. 1017–1021, 1993.
Ann of Intern. Med., vol. 114, pp. 216–223, 1991.

*Primary Examiner*—James H. Reamer
*Attorney, Agent, or Firm*—John P. White; Cooper & Dunham LLP

[57] ABSTRACT

The subject invention provides a method of treating a symptom associated with chronic obstructive pulmonary disease in a patient suffering from chronic obstructive pulmonary disease which comprises administering a therapeutically effective amount of an oxandrolone to the patient. The subject invention further provides a method of improving functional capacity and/or pulmonary function in a patient suffering from chronic obstructive pulmonary disease which comprises administering a therapeutically effective amount of an oxandrolone to the patient.

15 Claims, No Drawings

USE OF OXANDROLONE IN THE TREATMENT OF CHRONIC OBSTRUCTIVE PULMONARY DISEASE

This application claims priority of U.S. Provisional application Ser. No. 60/032,107, filed Dec. 5, 1996, the contents of which are hereby incorporated into this application by reference.

Throughout this specification, various publications are referenced by Arabic numerals within parentheses. Full citations for these references may be found at the end of the specification immediately preceding the claims. The disclosure of these publications in their entireties are hereby incorporated by reference into this specification in order to more fully describe the state of the art to which this invention pertains.

BACKGROUND OF THE INVENTION

Chronic Obstructive Pulmonary Disease (COPD)

COPD is a progressively debilitating disease affecting an estimated 16 million Americans. In 1984, COPD ranked fifth as the leading cause of death in the United States. From a disability standpoint, COPD is the most frequent reason that people seek medical attention (1).

It has been found that there is a direct relationship between body weight and respiratory muscle mass (2) and that a significant percentage of patients with COPD are malnourished (1, 2). Epidemiologic surveys of COPD have suggested that undernutrition might be an important prognostic variable (2). When the COPD patient begins to lose weight, the average life expectancy is only 2.9 years (1).

Disabilities in patients with COPD due to limitations in pulmonary function are often compounded by a loss of muscle strength and lean body mass, resulting in an inability to perform many activities of daily living. These losses may be attributable to a number of factors including decreased ability to exercise, decreased appetite, hypermetabolism and protein catabolism resulting from prolonged glucocortoid therapy. Because of undue dyspnea, these patients are frequently afraid to exercise, which exacerbates their muscle wasting condition. Shortness of breath during eating also worsens this condition because it leads to inadequate calorie and protein intake. Furthermore, many of these patients are receiving intermittent or chronic treatment with anti-inflammatory steroids that may result in myopathy, especially causing weakness in the proximal lower extremities. A combination of these factors often contribute to disability in patients with COPD that exceeds what would generally be expected based on airflow limitation alone.

Because of the progressive decline due to dyspnea and cachexia in these patients, levels of morbidity and mortality exceed those expected based on pulmonary limitations alone.

The subject invention provides therapies to reverse or halt the catabolic process and restore lean body mass in COPD patients. The subject invention also provides therapies to improve functional capacity and/or pulmonary function in these patients.

Adult Respiratory Distress Syndrome (ARDS)

ARDS consists of respiratory failure associated with various acute pulmonary injuries and is characterized by noncardiogenic pulmonary edema, respiratory distress and hypoxemia.

ARDS may be caused by a variety of pulmonary or systemic insults but is particularly frequent in patients with sepsis. Although termed "adult", ARDS occurs in children as well as adults.

Oxandrolone

Oxandrolone (17-methyl-17-hydroxy-2-oxa-5-androstan-3-one) is a known compound which is commercially available. The preparation of oxandrolone is described, inter alia, in U.S. Pat. No. 3,128,283. Oxandrolone is an anabolic steroid synthetically derived from testosterone. Oxandrolone has a unique chemical structure compared with other testosterone analogs. Oxandrolone contains an oxygen rather than a carbon atom at the 2-position within the phenanthrene nucleus (3) and lacks a 4-ene function in the A-ring. The anabolic activity of oxandrolone is approximately 6 times greater than its androgenic activity and has been found to be 6.3 times greater than that of methyltestosterone (3).

Anabolic activity refers to the ability to cause nitrogen retention, promoting weight gain and increasing muscle strength. Androgenic activity refers to the ability to enhance male characteristics (i.e. secondary sex characteristics such as facial hairs and voice changes). Because of the high ratio of anabolic to androgenic activity, oxandrolone is less likely to cause adverse cosmetic consequences in women than many testosterone analogs.

Furthermore, in contrast to the majority of oral androgenic anabolic steroids (e.g. micronized testosterone, methyltestosterone, fluoxymesterone), oxandrolone undergoes relatively little hepatic metabolism (4, 5).

Oxandrolone has been administered to malnourished patients with alcoholic hepatitis (6, 7). Oxandrolone has been shown to be safe even in dosages of up to 80 mg/day in patients with alcoholic hepatitis (6).

The subject invention discloses the use of an oxandrolone for the treatment of symptoms associated with chronic obstructive pulmonary disease and symptoms associated with ARDS.

SUMMARY OF THE INVENTION

The subject invention provides a method of treating a symptom associated with chronic obstructive pulmonary disease in a patient suffering from chronic obstructive pulmonary disease which comprises administering a therapeutically effective amount of an oxandrolone to the patient.

The subject invention further provides a method of improving functional capacity and/or pulmonary function in a patient suffering from chronic obstructive pulmonary disease which comprises administering a therapeutically effective amount of an oxandrolone to the patient.

DETAILED DESCRIPTION OF THE INVENTION

Oxandrolone as used herein encompasses 17-methyl-17-hydroxy-2-oxa-5-androstan-3-one (both racemic mixtures and optically active enantiomers) as well as pharmaceutically acceptable esters thereof. For example, an oxandrolone product which is commercially available is the Oxandrin® tablet from BTG Pharmaceuticals Corp., Iselin, N.J. 08830, which is 17α-methyl-17β-hydroxy-2-oxa-5α-androstan-3-one. This product was used throughout the studies described herein.

Oxandrolone may be administered orally, intravenously, intramuscularly, subcutaneously, topically, intratracheally, intrathecally, intraperitoneally, rectally, vaginally or intrapleurally.

If oxandrolone is administered orally, it is administered in the form of a tablet, a pill, a liquid or a capsule.

A liquid may be administered in the form of a solution or a suspension.

The compositions produced in accordance with the invention may comprise conventional pharmaceutically acceptable diluents or carriers. Tablets, pills, liquids and capsules may include conventional excipients such as lactose, starch, cellulose derivatives, hydroxypropyl methylcellulpse and magnesium stearate. Suppositories may include excipients such as waxes and glycerol. Injectable solutions will comprise sterile pyrogen-free media such as saline and may include buffering agents, stabilizing agents, solubilizing agents or preservatives. Conventional enteric coatings may also be used.

Compositions for topical administration may be in the form of creams, ointments, lotions, solutions, transdermal delivery systems, transdermal patches or gels.

The subject invention provides a method of treating a symptom associated with chronic obstructive pulmonary disease in a patient suffering from chronic obstructive pulmonary disease which comprises administering a therapeutically effective amount of an oxandrolone to the patient.

The symptom may inter alia be cachexia, muscle wasting, involuntary weight loss.

The subject invention further provides a method of improving pulmonary function in a patient suffering from chronic obstructive pulmonary disease which comprises administering a therapeutically effective amount of an oxandrolone to the patient.

The subject invention also provides a method of improving functional capacity and/or functional status and/or exercise capacity in a patient suffering from chronic obstructive pulmonary disease which comprises administering a therapeutically effective amount of an oxandrolone to the patient.

Functional capacity may be tested by the ability to carry out the activities of daily living such as walking, doing housework, carrying groceries, and may also be tested by exercise tolerance, ambulatory status, increased energy or increased mobility inter alia. Functional status and/or exercise capacity are tested in the same manner.

The subject invention also provides a use of an oxandrolone in the preparation of a composition to treat a symptom associated with COPD or to improve functional capacity and/or pulmonary function in a patient suffering from COPD.

In a preferred embodiment, the amount of the oxandrolone is about 10–20 mg per day.

In especially preferred embodiments, the amount of the oxandrolone is about 0.2 mg/kg per day.

Oxandrolone may be administered in a solid dosage form, in a liquid dosage form, in a sustained-release formulation or in a once a day formulation. The liquid dosage form may inter alia be alcohol-based or formulated with a cyclodextrin such as hydroxypropyl-$\beta$-cyclodextrin.

Interferon as used herein encompasses any interferon such as alpha-interferon, beta-interferon or gamma-interferon.

Corticosteroid as used herein encompasses inter alia glucocorticoids, mineralcorticoids and androgens. Examples of glucocorticoids are hydrocortisone, cortisone, corticosterone and synthetic analogs of hydrocortisone and cortisone (such as cortisol, prednisolone and prednisone). Examples of mineralcorticoids are aldosterone and desoxycorticosterone. Examples of androgens are DHEA, androstenedione, testosterone and 11$\beta$-hydroxyandrostenedione.

Oxandrolone may be administered in conjunction with an interferon, a corticosteroid or any known anti-inflammatory agent.

Oxandrolone may also be administered in conjunction with glutamine or human growth hormone.

The subject invention also provides a method of improving functional capacity and/or pulmonary function in a patient suffering from adult respiratory distress syndrome which comprises administering a therapeutically effective amount of an oxandrolone to the patient.

EXAMPLE

The Example which follows is set forth to aid in understanding the invention but is not intended to, and should not be construed to, limit its scope in any way.

The effect of oxandrolone in the treatment in a group of patients with COPD in reversing or stabilizing their progressive decline in pulmonary function, functional capacity and body weight, by increasing lean body mass and proximal muscle strength A study on the effect of oxandrolone on patients with COPD was performed as follows.

Patient characteristics

Eighteen (18) patients (11 women and 7 men), ranging in age from 47–77 who had a pulmonary function ($FEV_1$) of less than 50% of predicted normal according to their size and age, were included in this study. Patients served as their own controls. Of the 18 patients enrolled, 17 completed the study. One patient declined to continue participation after carefully reading the consent form and did not receive treatment with oxandrolone. None of the patients stopped taking the drug because of adverse effects.

Study design 17 patients received 0.2 mg/kg/day of oxandrolone in a single dose for 8 weeks. Baseline values were obtained for pulmonary function, percentage of body fat, maximum oxygen consumption ($VO_2$max) and leg muscle strength. Total cholesterol and HDL levels were also determined as well as SGOT levels. Assessments were repeated at 5 and 10 weeks after treatment was initiated. Thus, the last assessment was 2 weeks after the last dose of oxandrolone.

Testing procedures

Med-Graphics equipment with Breeze software was used to assess pulmonary function. Percentage of body fat was determined by the infrared method using the Futrex 5000 body fat analyzer. $VO_2$max was evaluated based on a modified Balke protocol with collection of expired gases and breath-by-breath analysis on Med-Graphics metabolic cart. The Nautilus® leg extension machine was used to assess proximal leg muscle strength. Patients were asked to extend their legs bearing their maximum weight for six repetitions. Results were analyzed for statistical significance using the Student's t test.

Results

TABLE 1 effects of 8 weeks of oxandrolone therapy on lean body mass and muscle strength in patients with COPD.

| Parameters assessed | Before treatment with oxandrolone (0.2 mg/kg/d) | Follow-up, after Initiation of Oxandrolone Treatment (Week 10) | p value |
|---|---|---|---|
| Body weight (lbs) | 125.5 | 127.1 | NS |
| Body fat | 23.5 | 20.7 | <0.001 |

TABLE 1-continued effects of 8 weeks of oxandrolone therapy on lean
body mass and muscle strength in patients with COPD.

| Parameters assessed | Before treatment with oxandrolone (0.2 mg/kg/d) | Follow-up, after Initiation of Oxandrolone Treatment (Week 10) | p value |
| --- | --- | --- | --- |
| (%) | | | |
| $FEV_1$ | 1.07 | 1.12 | <0.01 |
| Proximal leg strength | 40.3 | 58.9 | <0.001 |
| Total cholesterol | 206 mg/DL | 205 | NS |
| HDL | 52.2 | 53.6 | NS |
| $VO_2max$ | 18.6 mL/min/m² | 21.8 | <0.001 |
| SGOT | 32 U/L | 32.4 | NS |

NS = not significant

As can be seen from Table 1, oxandrolone produced significant differences in percentage of body fat, leg extension muscle strength and $VO_2max$. There was a small insignificant increase in body weight. Body fat, however, was significantly decreased by 3% (p<0.001) suggesting an increase in lean body mass consistent with the anabolic effect of oxandrolone. The most significant improvement noted was in leg extension muscle strength. Maximum weight lifted upon leg extension increased from an average of 40.3 pounds to 58.9 pounds (p<0.001). Such a significant improvement in muscle strength allows patients greater and more efficient mobility that enables them to accomplish tasks of daily living with less distress.

Surprisingly, $VO_2max$ increased significantly from 18.6 to 21.8 mL/min/m² (p<0.001). $VO_2max$ is an excellent indicator of an individual's fitness level and quantitates ability to perform daily functions.

Notably, a subgroup of six patients with less severe pulmonary impairment at the onset of the study showed the most improvement. In these patients whose $VO_2max$ exceeded 17 at the onset of the trial, oxandrolone treatment increased $VO_2max$ from 19.4 to 24.2 mL/min/m². This may indicate that patients with moderate to severe pulmonary impairment may benefit more from oxandrolone therapy than patients with very severe impairment. At very severe levels of impairment, airflow may limit any improvement in $VO_2max$ regardless of the improvement in proximal muscle strength.

In addition, patients achieved a statistically significant improvement in $FEV_1$, with values increasing from 1.07 to 1.12 liters (p<0.01).

There were no significant differences in total cholesterol, HDL or SGOT levels and there were no reported adverse effects during this study.

The results of this study indicate that oxandrolone is a safe and effective treatment for symptoms associated with COPD.

References

1. Rose W. (1992), Journal of Intravenous Nursing 15(1): 18–23
2. Donahoe et al. (1990), Clinics in Chest Medicine 11(3): 487–504.
3. Fox et al. (1962), J. Clin. Endocrinol. Metab. 22: 921–924.
4. Karim et al. (1973), Clin. Pharmacol. Therap. 14: 862–869.
5. Masse et al. (1989), Biomedical and Environmental Mass Spectrometry 18:429–438.
6. Mendenhall et al. (1993), Hematology 17(4): 564–576.
7. Bonkovsky et al. (1991), The American Journal of Gastroenterology 86(9): 1209–1218.

What is claimed is:

1. A method of treating a symptom associated with chronic obstructive pulmonary disease in a patient suffering from chronic obstructive pulmonary disease which comprises administering a therapeutically effective amount of an oxandrolone to the patient.

2. A method according to claim 1, wherein the symptom is cachexia, muscle wasting or involuntary weight loss.

3. A method of improving pulmonary function in a patient suffering from chronic obstructive pulmonary disease which comprises administering a therapeutically effective amount of an oxandrolone to the patient.

4. A method of improving functional capacity in a patient suffering from chronic obstructive pulmonary disease which comprises administering a therapeutically effective amount of an oxandrolone to the patient.

5. A method according to claims 1, 3, or 4 wherein the amount of the oxandrolone is about 1–100 mg/day.

6. A method according to claim 5 wherein the amount of the oxandrolone is about 10–20 mg/day.

7. A method according to claim 5 wherein the amount of the oxandrolone is about 0.2 mg/kg/day.

8. A method according to claims 1, 3 or 4 wherein the oxandrolone is administered orally.

9. A method according to claims 1, 3, or 4 wherein the oxandrolone is injected.

10. A method according to claims 1, 3, or 4 wherein the oxandrolone is in a solid dosage form.

11. A method according to claims 1, 3, or 4 wherein the oxandrolone is in a liquid dosage form.

12. A method according to claims 1, 3, or 4 wherein the oxandrolone is in a sustained-release formulation.

13. A method of improving pulmonary function in a patient suffering from adult respiratory distress syndrome which comprises administering a therapeutically effective amount of an oxandrolone to the patient.

14. A method of improving functional capacity in a patient suffering from adult respiratory distress syndrome which comprises administering a therapeutically effective amount of an oxandrolone to the patient.

15. A method according to claims 1, 3, 4, 13 or 14, wherein the oxandrolone is 17α-methyl-17β-hydroxy-2-oxa-5α-androstan-3-one.

* * * * *